(12) United States Patent
Mohite et al.

(10) Patent No.: US 12,039,730 B2
(45) Date of Patent: Jul. 16, 2024

(54) METHOD AND SYSTEM FOR PLANT HEALTH ESTIMATION

(71) Applicant: Tata Consultancy Services Limited, Mumbai (IN)

(72) Inventors: Jayantrao Mohite, Thane West (IN); Sanjay Kimbahune, Thane West (IN); Srinivasu Pappula, Hyderabad (IN); Dineshkumar Singh, Thane West (IN); Sanat Sarangi, Thane West (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 0 days.

(21) Appl. No.: 17/372,725

(22) PCT Filed: Jan. 15, 2020

(86) PCT No.: PCT/IB2020/050288
§ 371 (c)(1),
(2) Date: Jul. 12, 2021

(87) PCT Pub. No.: WO2020/148661
PCT Pub. Date: Jul. 23, 2020

(65) Prior Publication Data
US 2024/0029254 A1    Jan. 25, 2024

(30) Foreign Application Priority Data
Jan. 15, 2019    (IN) .............................. 201921001768

(51) Int. Cl.
*G06K 9/00* (2022.01)
*G01N 33/00* (2006.01)
(Continued)

(52) U.S. Cl.
CPC ....... *G06T 7/0014* (2013.01); *G01N 33/0098* (2013.01); *G06V 10/762* (2022.01);
(Continued)

(58) Field of Classification Search
CPC .... G06V 20/188; G06V 20/13; G06V 10/762; G06T 2207/30188; G01N 33/0098
See application file for complete search history.

(56) References Cited

U.S. PATENT DOCUMENTS

2012/0109614 A1    5/2012    Lindores
2015/0278966 A1*  10/2015    Johnson ............... G06Q 10/063
                                                            702/2
(Continued)

FOREIGN PATENT DOCUMENTS

GB        2557469 A  *  6/2018  ............. A01D 91/02
WO    WO 2014/100856 A1    7/2014
WO    WO-2017062292 A1 *  4/2017  ........... A01B 79/005

OTHER PUBLICATIONS

Samborski, S. M., Tremblay, N., & Fallon, E. (2009). Strategies to make use of plant sensors-based diagnostic information for nitrogen recommendations. Agronomy journal, 101(4), 800-816. (Year: 2009).*

(Continued)

*Primary Examiner* — Andrew M Moyer
(74) *Attorney, Agent, or Firm* — FINNEGAN, HENDERSON, FARABOW, GARRETT & DUNNER LLP

(57) ABSTRACT

Plant health estimation is required to be performed so as to detect any health issues in early stages, so as to take counter measures. Existing systems for the plant health estimation perform the health estimation by considering data obtained from satellite images of the plants being monitored. However this alone may not be much effective as the satellite images fail to provide information on many parameters which have direct or indirect impact on health of the plants. Disclosed herein are a method and a system for plant health estimation, wherein the system performs health estimation at a macro level and a micro level. The macro level health estimation is done using satellite images of the plants as (Continued)

inputs, whereas the micro level health estimation is done by collecting and processing sensor data with respect to various parameters that affect health of a plant.

12 Claims, 4 Drawing Sheets

(51) Int. Cl.
  *G06T 7/00* (2017.01)
  *G06V 10/762* (2022.01)
  *G06V 20/10* (2022.01)
  *G06V 20/13* (2022.01)
  *G06V 20/90* (2022.01)

(52) U.S. Cl.
  CPC ............ *G06V 20/13* (2022.01); *G06V 20/188* (2022.01); *G06V 20/90* (2022.01); *G06T 2207/10032* (2013.01); *G06T 2207/30188* (2013.01)

(56) References Cited

U.S. PATENT DOCUMENTS

| | | |
|---|---|---|
| 2016/0003790 A1 | 1/2016 | Osborne et al. |
| 2016/0078375 A1 | 3/2016 | Ethington et al. |
| 2016/0217562 A1 | 7/2016 | Ulman |
| 2016/0247079 A1 | 8/2016 | Mewes et al. |
| 2018/0059691 A1 | 3/2018 | Fleming et al. |
| 2018/0108123 A1 | 4/2018 | Baurer et al. |
| 2018/0330247 A1* | 11/2018 | Cohen .................... G06F 30/20 |

OTHER PUBLICATIONS

Inoue, Y., Sakaiya, E., & Wang, C. (2014). Capability of C-band backscattering coefficients from high-resolution satellite SAR sensors to assess biophysical variables in paddy rice. Remote Sensing of Environment, 140, 257-266. (Year: 2014).*

Liu, H., Whiting, M. L., Ustin, S. L., Zarco-Tejada, P. J., Huffman, T., & Zhang, X. (2018). Maximizing the relationship of yield to site-specific management zones with object-oriented segmentation of hyperspectral images. Precision agriculture, 19, 348-364. (Year: 2018).*

Kuwata et al., "Precise agricultural monitoring based on sensor network and satellite remote sensing: Saving water usage of orchards in California," J Remote Sensing & GIS 2017, 6:3(Suppl) (2020).

Shekhar et al., "Intelligent Infrastructure for Smart Agriculture: An Integrated Food, Energy and Water System," Computing Community Consortium Catalyst (2017).

Tangpattanakul et al., "A study of rice phenological development stages estimation from field server images," (2015).

* cited by examiner

METHOD AND SYSTEM FOR PLANT HEALTH ESTIMATION

CROSS-REFERENCE TO RELATED APPLICATIONS AND PRIORITY

The present application is a national stage application of PCT/IB2020/050288, which claims priority to India Patent Application No. 201921001768, filed before Indian Patent Office on Jan. 15, 2019. Entire contents of the aforementioned applications are incorporated herein by reference.

TECHNICAL FIELD

The disclosure herein generally relates to plant health estimation, and, more particularly, to a method and system for plant health estimation involving a macro level estimation and a micro level estimation.

BACKGROUND

There are various factors that affect health of plants. For example, there may be insects which attack the plants and cause damage. Similarly, various other factors such as climate condition, pollution, and so on also can adversely affect health of the plants. Often symptoms develop on the plants which indicate/represent one or more health conditions of the plants. If such symptoms are noticed in early stages, then accordingly some remedies can be taken by the farmers. However, when the plants are planted over a wide area, it becomes difficult for a user (a farmer) to manually inspect and identify such symptoms.

There exist a few systems which can perform plant health estimation. Some of such systems use satellites to capture images and other data pertaining to plants being monitored for gathering information pertaining to the plants being monitored. Some of the existing systems use different types of sensors to collect data. Such data are used by the systems to identify health of the plants. However, disadvantage of the existing systems is that the use of different types of data is not streamlined.

SUMMARY

Embodiments of the present disclosure present technological improvements as solutions to one or more of the above-mentioned technical problems recognized by the inventors in conventional systems. For example, in one embodiment, a processor-implemented method for plant health estimation is provided. Initially a plurality of satellite images of one or more fields where a plurality of plants being monitored are located are collected via one or more hardware processors. Further, at least one sensor data pertaining to at least one parameter affecting health of each of the plurality of plants being monitored is collected, via the one or more hardware processors. Further, a macro level health of each plant in a sample set of plants from the plurality of plants is estimated, using at least one of the plurality of satellite images, via the one or more hardware processors. While estimating the macro level health, the at least one satellite image is processed with a plant spectral behavioral data to generate at least one start of the season (SoS) information corresponding to the sample set of plants. Then the sample set of plants is clustered to a plurality of clusters, based on the start of the season information and a plant area information, via the one or more hardware processors, and then the macro level health is estimated for each of the plurality of clusters. Then a micro level health of each plant in the sample set of plants is estimated using the at least one sensor data, via the one or more hardware processors, wherein the micro level health is estimated at a plant level. Further, the macro level health is updated based on the corresponding micro level health.

In another aspect, a system for plant health estimation is provided. The system includes one or more communication interfaces (103), one or more hardware processors (102), and one or more memory modules (101) storing a plurality of instructions. The plurality of instructions, when executed, cause the one or more hardware processors to: collect a plurality of satellite images of one or more fields where a plurality of plants being monitored are located; collect at least one sensor data pertaining to at least one parameter affecting health of the plants being monitored; estimate a macro level health of each plant in a sample set of plants, using at least one of the plurality of satellite images, comprising: processing the at least one of the plurality of satellite images with a plant spectral behavioral data to generate at least one start of the season (SoS) information corresponding to the sample set of plants; clustering the sample set of plants to a plurality of clusters, based on the start of the season information and a plant area information; and estimating the macro level health for each of the plurality of clusters. The system then estimates a micro level health of each plant in the sample set of plants using the at least one sensor data and then updates the macro level health of the each plant in the sample set of plants based on the corresponding micro level health.

In yet another aspect, a non-transitory computer readable medium for plant health estimation is provided. Initially a plurality of satellite images of one or more fields where a plurality of plants being monitored are located are collected via one or more hardware processors. Further, at least one sensor data pertaining to at least one parameter affecting health of each of the plurality of plants being monitored is collected, via the one or more hardware processors. Further, a macro level health of each plant in a sample set of plants from the plurality of plants is estimated, using at least one of the plurality of satellite images, via the one or more hardware processors. While estimating the macro level health, the at least one satellite image is processed with a plant spectral behavioral data to generate at least one start of the season (SoS) information corresponding to the sample set of plants. Then the sample set of plants is clustered to a plurality of clusters, based on the start of the season information and a plant area information, via the one or more hardware processors, and then the macro level health is estimated for each of the plurality of clusters. Then a micro level health of each plant in the sample set of plants is estimated using the at least one sensor data, via the one or more hardware processors, wherein the micro level health is estimated at a plant level. Further, the macro level health is updated based on the corresponding micro level health.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
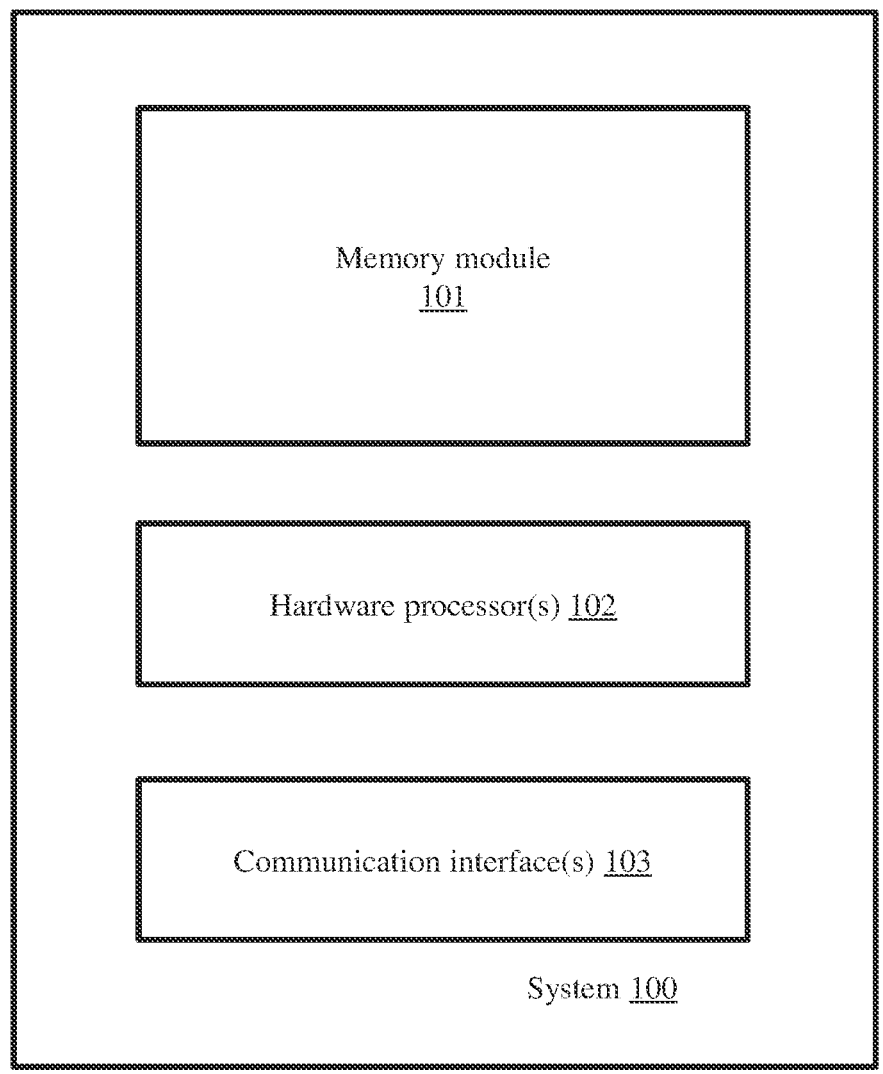
FIG. 1 illustrates an exemplary block diagram of a system for performing plant health estimation, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

FIG. 1 illustrates an exemplary block diagram of a system for performing plant health estimation, according to some embodiments of the present disclosure. The system 100 includes a memory module 101, one or more hardware processors 102, and one or more communication interfaces 103.

The memory module(s) 101 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory module(s) 101. The memory module(s) 101 are further configured to store a plurality of instructions, which when executed, cause the one or more hardware processor(s) 102 to perform different actions associated with the plant health estimation being handled by the system 100. The memory module(s) 101 can be further configured to store any data, associated with the health estimation, for example, reference data pertaining to plant type, Start of the Season (SoS) information, plant type, sensor data weightage and so on, which are used by the system 100 to perform the plant health assessment. The memory module 101 can be further configured to store data pertaining to an estimated health of the plants as reference data.

The one or more hardware processors 102 can be implemented as one or more processors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like. The one or more hardware processors 102 are configured to perform data and control signal processing, at different stages of the plant health estimation, as required.

The communication interface(s) 103 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the communication interface(s) 103 can include one or more ports for connecting a number of devices to one another or to another server. The communication interface(s) can be configured to provide one or more channels with appropriate protocols, for the system 100 to communicate with one or more external systems. For example, the communication interface(s) 103 interacts with at least one image capturing means (a satellite) for collecting the image(s) of the plants being monitored. Similarly, the communication interface(s) 103 provides at least one suitable channel/interface to communicate with at least one sensor to collect the sensor inputs with respect to different parameters being monitored for the purpose of health estimation.

The system 100 executes the following steps during the health estimation of plants:

The system 100 collects one or more satellite images of a geographical area where fields in which a plurality of plants being monitored are located, as input. The system 100 further collects, using one or more associated sensors, data pertaining to one or more parameters that impact health of the plants, as input. For example, data pertaining to parameters such as but not limited to soil moisture, leaf nitrogen level, and chlorophyll are collected using appropriate sensors. In an embodiment, based on type of data required for the health estimation, any suitable type of sensors can be used by the system 100.

The system 100 stores early system time series data as a reference data in the memory module 101. The early system time series data may refer to data corresponding to plants, plant area, crop information, and so on, that may have been collected by the system 100 over a period of time. This information is updated to reflect/capture any change to the data captured and stored as the early system time series data. The system 100 refers to this data for plant area estimation. The plant area information is then processed by the system 100, using any appropriate machine learning technique, to identify target plant, wherein the target plant refers to the plant(s) to be monitored by the system 100 for health estimation. At this stage, the system 100 identifies pixels in the one or more satellite images that are to be considered for the health estimation.

The system 100 further estimates Start of the Season (SoS) information pertaining to the plants being monitored. The SoS information represents when the plants have been planted, and in turn provides information on age/growth stage of the plants. For the purpose of estimating the SoS information, the system 100 stores backscatter value (during a time period) for each pixel in each satellite image being processed, and corresponding date, in a key-value pair format i.e. like Sv1-Sd1, Sv2-Sd2, . . . Svt-Sdt). Then the system identifies minimum value among the backscatter values stored i.e. MinV=min (Sv1, Sv2, . . . Svt). After identifying the minimum value, the system 100 checks the corresponding date, and this date is the SoS information for the pixel being considered. This process is repeated for all the pixels being considered.

For example, assume that for a rice plant, during a transplanting window between July-August, 2018, the backscatter values-corresponding date pairs are: (−9.1-184, −9.8-196, −13-208, −12.1-220, −10.22-232, −9.76-244)

Where the values 184, 196, 208, 220, 232, and 244 represents date stored in day of the year (DoY) format. Here the minimum value MinV=−13, and the corresponding SoS is 208 i.e. 27 Jul. 2018.

Then the system 100 estimates a macro level health of the plant(s) being monitored. Steps are given below:

Macro Level Health Estimation:

At this stage, the system 100 clusters the sample set of plants to a plurality of clusters, based on corresponding SoS information and a plant area information. Then the system 100 identifies, for each SoS, for each plant in a sample set of plants, one or more indices. In an embodiment, data pertaining to the one or more indices to be considered for the plant is identified based on data in a reference database which specifies the indices matching each plant (or plant type), along with other information.

The system 100 uses this information pertaining to the SoS and value of each of the indices considered, to generate a health index value for the SoS. This step is repeated for all the pixels being considered, and the health index values are normalized between 0 and 1. Then the system 100 identifies values closer to 0 as indicating poor health of the plants and values closer to 1 as indicating good health.

For example, consider that NDVI and NDWI are two indices for rice plant. For SoS 208 (i.e. Jul. 27, 2018), for a pixel, NDVI (t2)=0.34. NDVI (t1)=0.29, and NDWI (t2)=0.33. NDWI (t1)=0.31. then the macro level health is estimated as:

$$\text{Health } (m)=(0.5*(NDVIt2-NDVIt1))+(0.5*(NDWIt2-NDWIt1))=0.035 \quad (1)$$

This process is repeated for all the pixels to estimate the macro level health. It is also required to note that the equation 1 can be generalized and can be used for any indices and corresponding values of the indices. The macro level health is estimated at a field level/plot level i.e. the macro level health represents health of a group/a plurality of plants.

Then the system 100 estimates micro level health of the plants. Process of estimating the micro level health is explained below:

Micro Level Health Estimation:

At this stage, the system 100 identifies sensors to be considered for a plant and corresponding weightages to be assigned, based on data in a reference database. The reference database contains information pertaining to plant types and corresponding sensors and weightages. This information may be pre-configured or dynamically configured with the memory module 101.

After identifying the weightages for each sensor data being considered, the system 100 estimates the micro level health of the plants as a function of the weightages, sensor data from each sensor being considered, plant type, and the information pertaining to growth stage of the plant, as:

$$\text{Health}(M)=f(\text{plant},\text{growth stage},w1*s1,w2*s2, \ldots wn*sn) \quad (2)$$

Consider the example below:

Table 1 shows weightages of different sensors at different growth stages of the rice plant:

TABLE 1

|  | Transplanting | Tillering | Panicle initiation | Flowering | Upto harvest |
|---|---|---|---|---|---|
| Soil Moisture (SM) | 0.75 | 0.2 | 0.2 | 0.15 | 0.25 |
| LAI | 0.15 | 0.3 | 0.3 | 0.35 | 0.25 |
| Leaf nitrogen | 0.05 | 0.25 | 0.2 | 0.2 | 0.25 |
| Chlorophyll | 0.05 | 0.25 | 0.3 | 0.30 | 0.25 |

If weightages are to be picked for tillering phase, and assuming that values of the sensors are SM=34%, LAI=2.1, leaf nitrogen=25 mg/g, and chlorophyll=10 mg/g, the micro level health is calculated as:

$$\text{Health }(M)=((0.2*0.7)+(0.3*0.5)+(0.25*0.78)+(0.25*0.85))=0.6975$$

Based on the estimated micro level health of the plants, the macro level health is updated, and the updated macro level health represents the health of the corresponding cluster of plants.

The system 100 may use any suitable model to update the macro level health using the micro level health data. An example of the model used for updating the micro level health using the macro level health information is given below:

$$\text{Health }(m)=0.15*\text{Health }(M)+0.41 \quad (3)$$

where the values 0.15 and 0.41 are sample micro level health data points, which can be changed as per requirements and/or other parameters such as plant type, sensor type and so on.

Similarly, an example of the model for temporal updation of micro level health of the plants is given below:

Consider that time series of the micro level health as Health (M)t1, Health (M)t2, Health(M)t3, Health(M)t4

Consider that time series of the macro level health as Health(m)t1, Health(m)t2, Health(m)t3, Health(m)t4 then, $$\text{Health}(M)t5=f(\text{Health}(M)t1,\text{Health}(M)t2,\text{Health}(M)t3,\text{Health}(M)t4) \text{ and } f(\text{Health}(m)t1,\text{Health}(m)t2,\text{Health}(m)t3,\text{Health}(m)t4) \quad (4)$$

This model can be used to update micro level health data for all pixels for which micro level health data is not available and macro level health data is available. In some scenarios, the micro level health data may not be available, or the macro level health data may not be available. In such scenarios, the system 100 uses appropriate data models (as in equation 3, and/or equation 4) that establish relation between the micro level health and the macro level health, so as to update the micro level health using the macro level health information or vice-versa. The updated macro level health data (and the micro level health data separately if needed) can be provided to one or more end users. For example, the users (who may be operator of the system, consumers such as farmers, and any other interested person) may opt to receive notifications regarding the health status of the plants being monitored, and such users may be notified of the estimated plant health (macro level and/or micro level health) using any suitable mechanism such as but not limited to Short Message Service (SMS), emails, voice messages, and so on, periodically/as and when the health estimation is being performed by the system 100. In another example, a dedicated mobile application with an appropriate User Interface may be provided to the users for real-time tracking of the plant health.

Further, by taking into account the data obtained from the satellite images as well as the sensor data, the system 100 is able to perform the health estimation using multiple parameters/factors that directly/indirectly affect health of the plants, which in turn results in improving accuracy of the health estimation.

Figure 2:
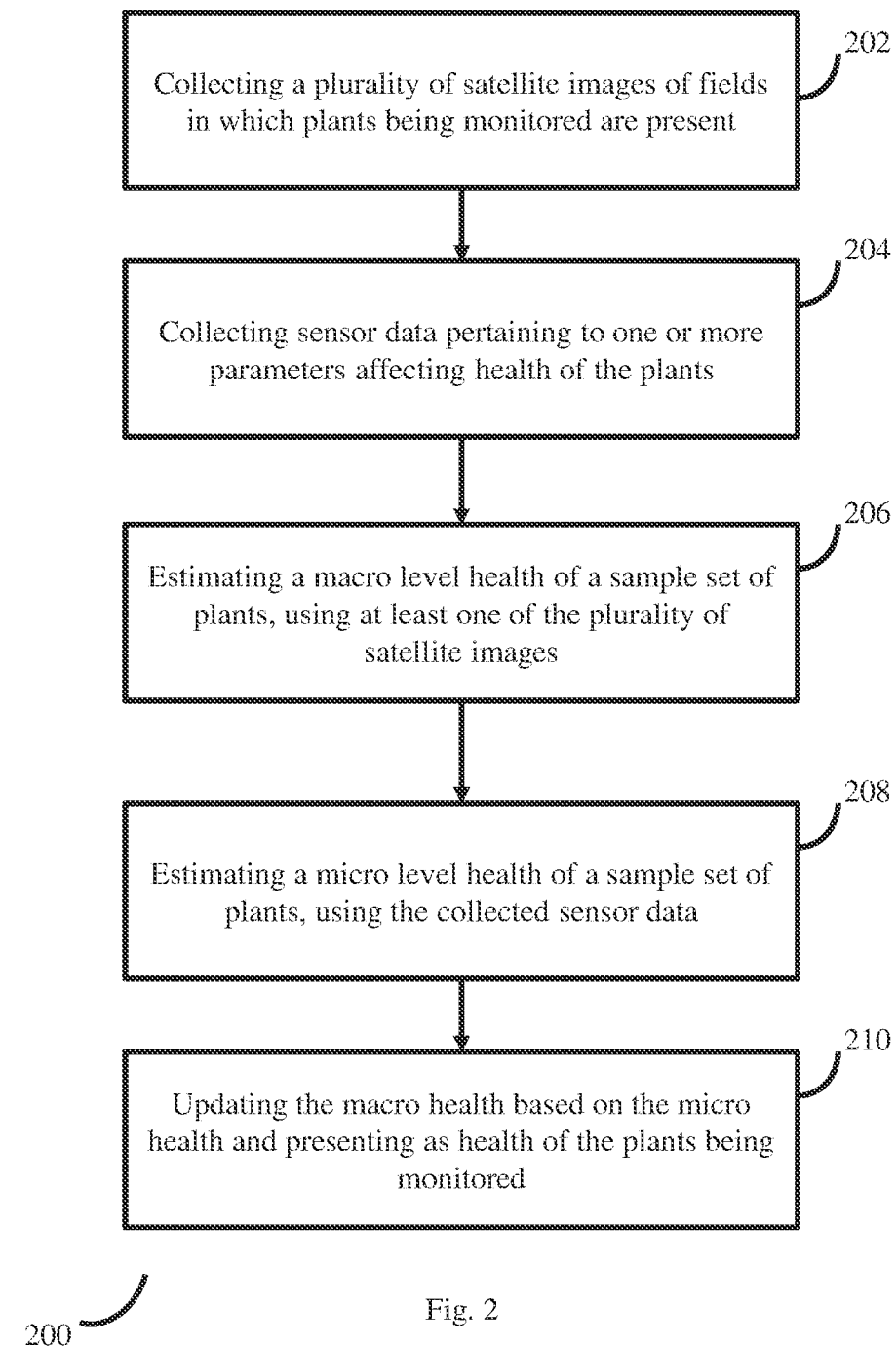
FIG. 2 is a flow diagram depicting steps involved in the process of performing health estimation of plants, using the system of FIG. 1, according to some embodiments of the present disclosure.

FIG. 2 is a flow diagram depicting steps involved in the process of performing health estimation of plants, using the system of FIG. 1, according to some embodiments of the present disclosure. The system 100 collects (202) a plurality of satellite images of one or more fields in which plants being monitored for health estimation are located. The system 100 further collects (204) sensor data pertaining to one or more parameters that affect health of the plants being monitored, using one or more appropriate sensors.

The system 100 then estimates (206) a macro level health of each of the plants being monitored, using the one or more satellite images and other related information. The system 100 further estimates (208) a micro level health of each of the plants being monitored, using the sensor data collected and other related information. The macro level health data and the micro level health data collectively represent (210) health of the plants.

Figure 3:
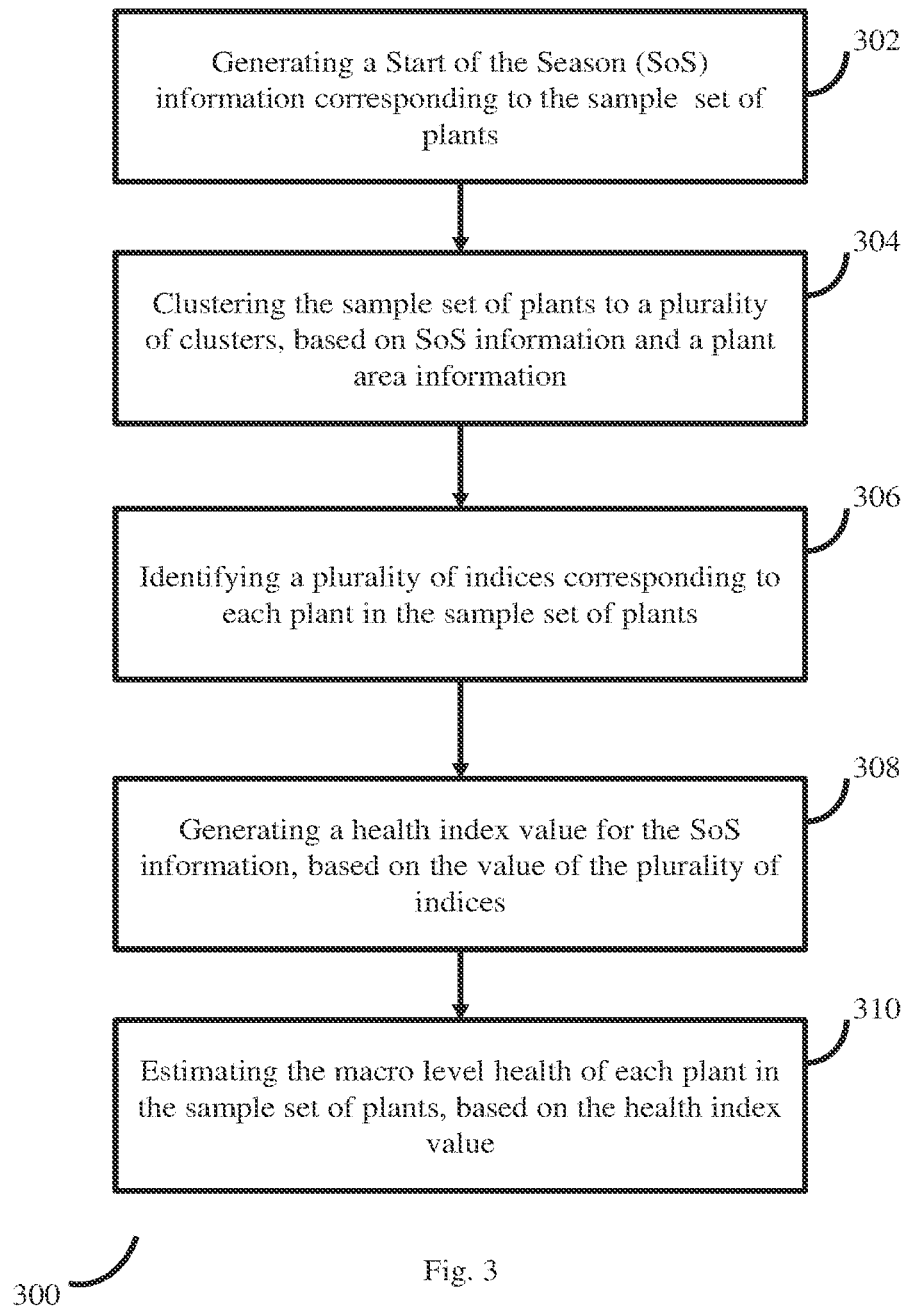
FIG. 3 is a flow diagram depicting steps involved in the process of estimating macro level health of plants, using the system of FIG. 1, according to some embodiments of the present disclosure.

FIG. 3 is a flow diagram depicting steps involved in the process of estimating macro level health of plants, using the system of FIG. 1, according to some embodiments of the present disclosure. In this process, the system 100 initially generates (302) a Start of the Season (SoS) information corresponding to the sample set of plants. The system 100 then clusters (304) the sample set of plants to a plurality of clusters, based on the SoS information and a plant area information. The system 100 then identifies (306) a plurality of indices corresponding to each plant in the sample set of plants, based on a pre-configured or dynamically configured reference data. The system 100 then generates (308) a health index value for the SoS information, based on the value of the plurality of indices. Further the system 100 estimates the macro level health of each of the plants, based on the health index value.

Figure 4:
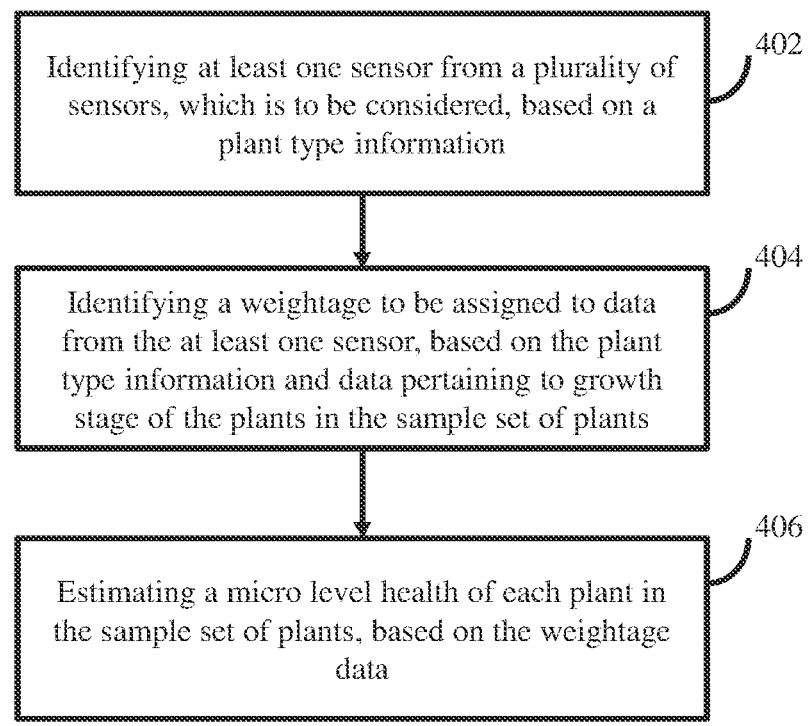
FIG. 4 is a flow diagram depicting steps involved in the process of estimating micro level health of plants, using the system of FIG. 1, according to some embodiments of the present disclosure.

FIG. 4 is a flow diagram depicting steps involved in the process of estimating micro level health of plants, using the system of FIG. 1, according to some embodiments of the present disclosure. The system 100 identifies (402) at least one sensor which is relevant to a plant being considered, from a plurality of sensors, as the sensor to be considered. In an embodiment, the system 100 identifies the at least one sensor to be considered, based on a reference data. Further the system 100 identifies (404) weightage of the at least one sensor considered, for a plant growth stage during which the health estimation is being performed. Data from the at least one sensor being considered, and the corresponding weightage data are used by the system 100 to estimate (406) the micro level health of each of the plants.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of health estimation of plants. The embodiment, thus provides a mechanism for micro level health estimation using sensor data and macro level health estimation using satellite image data. Moreover, the embodiments herein further provide models for updating macro level health data and micro level health data.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one processor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

The invention claimed is:

1. A processor-implemented method for plant health estimation, comprising:
    collecting a plurality of satellite images of one or more fields where a plurality of plants being monitored are located, via one or more hardware processors;
    collecting at least one sensor data pertaining to at least one parameter affecting health of each of the plurality of plants being monitored, via the one or more hardware processors, wherein the at least one parameter comprises soil moisture, leaf nitrogen level, and chlorophyll collected using multiple sensors;
    estimating a macro level health of each plant in a sample set of plants from the plurality of plants, using at least one of the plurality of satellite images, via the one or more hardware processors, comprising:
        processing the at least one satellite image with a plant spectral behavioral data to generate at least one start of the season (SoS) information corresponding to the sample set of plants, wherein the SoS information represents age and growth stage of the sample set of plants, and wherein the SoS information is generated by:
            storing a backscatter value for each pixel of each of the at least one satellite image being processed during a time period, and a corresponding date, in a key-value pair format;
            identifying a minimum value among the stored backscatter values;
            checking the corresponding date, after identifying the minimum value, as date for the SoS information for the pixel being considered; and
            repeating the steps of storing, identifying and checking, to generate the SoS information for all the pixels of each of the at least one satellite image;
        clustering the sample set of plants to a plurality of clusters, based on the start of the season information and a plant area information, via the one or more hardware processors; and
        estimating the macro level health for each of the plurality of clusters;
    estimating a micro level health of the each plant in the sample set of plants using the at least one sensor data, via the one or more hardware processors, wherein the micro level health is estimated at a plant level; and
    updating the macro level health of the each plant in the sample set of plants based on the corresponding micro level health.

2. The method as claimed in claim 1, wherein estimating the macro level health for each of the plurality of clusters comprises:
    identifying a plurality of indices corresponding to plants in each of the plurality of clusters, via the one or more hardware processors;
    generating a health index value for the at least one SOS information based on value of each of the plurality of indices, via the one or more hardware processors;
    comparing the health index value with a threshold range of reference data, via the one or more hardware processors; and
    estimating the macro level health of each of the plurality of clusters of plants based on the comparison of the health index value with the threshold range of reference data, via the one or more hardware processors, wherein the health index values are normalized between 0 and 1, and wherein the micro level health is estimated as indicating poor health when the health index values are closer to 0, and the micro level health is estimated as indicating good health when the health index values are closer to 1.

3. The method as claimed in claim 1, wherein estimating the micro level health comprises:
    identifying at least one sensor which is to be considered, based on a plant type information pertaining to the plants in the sample set of plants, via the one or more hardware processors;
    identifying a weightage to be assigned to data from the at least one sensor, based on the plant type information and data pertaining to growth stage of the plants in the sample set of plants, via the one or more hardware processors; and
    estimating the micro level health of each plant in the sample set of plants, based on the weightage assigned to each of the plurality of parameters, via the one or more hardware processors.

4. The method as claimed in claim 1, wherein the growth stage of the sample set of plants comprises Transplanting, Tillering, Panicle initiation, Flowering and up to harvesting.

5. A system for plant health estimation, comprising:
    one or more communication interfaces;
    one or more hardware processors; and
    one or more memory storing a plurality of instructions, wherein said plurality of instructions, when executed, cause the one or more hardware processors to:
        collect a plurality of satellite images of one or more fields where a plurality of plants being monitored are located;
        collect at least one sensor data pertaining to at least one parameter affecting health of the plants being monitored, wherein the at least one parameter comprises soil moisture, leaf nitrogen level, and chlorophyll collected using multiple sensors;
        estimate a macro level health of each plant in a sample set of plants, using at least one of the plurality of satellite images, comprising:
            processing the at least one of the plurality of satellite images with a plant spectral behavioral data to generate at least one start of the season (SoS) information corresponding to the sample set of plants, wherein the SoS information represents age and growth stage of the sample set of plants, and wherein the SoS information is generated by:

storing a backscatter value for each pixel of each of the at least one satellite image being processed during a time period, and a corresponding date, in a key-value pair format;

identifying a minimum value among the stored backscatter values;

checking the corresponding date, after identifying the minimum value, as date for the SoS information for the pixel being considered; and repeating the steps of storing, identifying and checking, to generate the SoS information for all the pixels of each of the at least one satellite image;

clustering the sample set of plants to a plurality of clusters, based on the start of the season information and a plant area information; and estimating the macro level health for each of the plurality of clusters;

estimate a micro level health of the each plant in the sample set of plants using the at least one sensor data; and update the macro level health of the each plant in the sample set of plants based on the corresponding micro level health.

6. The system as claimed in claim 5, wherein the system estimates the macro level health by:

identifying a plurality of indices corresponding to plants in each of the plurality of clusters;

generating a health index value for the at least one SoS information based on value of each of the plurality of indices;

comparing the health index value with a threshold range of reference data; and estimating the macro level health of each of the plurality of clusters of plants based on the comparison of the health index value with the threshold range of reference data, wherein the health index values are normalized between 0 and 1, and wherein the micro level health is estimated as indicating poor health when the health index values are closer to 0, and the micro level health is estimated as indicating good health when the health index values are closer to 1.

7. The system as claimed in claim 5, wherein the system estimates the micro level health by:

identifying at least one sensor which is to be considered, based on a plant type information pertaining to the plants in the plant set;

identifying a weightage to be assigned to data from the at least one sensor, based on the plant type information and data pertaining to growth stage of the plants in the plant set; and estimating the micro level health of the sample set of plants based on the weightage assigned to each of the plurality of parameters.

8. The system as claimed in claim 5, wherein the growth stage of the sample set of plants comprises Transplanting, Tillering, Panicle initiation, Flowering and up to harvesting.

9. A non-transitory computer readable medium for plant health estimation, the non-transitory computer readable medium performing the plant health estimation by:

collecting a plurality of satellite images of one or more fields where a plurality of plants being monitored are located, via one or more hardware processors;

collecting at least one sensor data pertaining to at least one parameter affecting health of each of the plurality of plants being monitored, via the one or more hardware processors, wherein the at least one parameter comprises soil moisture, leaf nitrogen level, and chlorophyll collected using multiple sensors;

estimating a macro level health of each plant in a sample set of plants from the plurality of plants, using at least one of the plurality of satellite images, via the one or more hardware processors, comprising:

processing the at least one satellite image with a plant spectral behavioral data to generate at least one start of the season (SoS) information corresponding to the sample set of plants, wherein the SoS information represents age and growth stage of the sample set of plants, and wherein the SoS information is generated by:

storing a backscatter value for each pixel of each of the at least one satellite image being processed during a time period, and a corresponding date, in a key-value pair format;

identifying a minimum value among the stored backscatter values;

checking the corresponding date, after identifying the minimum value, as date for the SoS information for the pixel being considered; and repeating the steps of storing, identifying and checking, to generate the SoS information for all the pixels of each of the at least one satellite image;

clustering the sample set of plants to a plurality of clusters, based on the start of the season information and a plant area information, via the one or more hardware processors; and estimating the macro level health for each of the plurality of clusters;

estimating a micro level health of the each plant in the sample set of plants using the at least one sensor data, via the one or more hardware processors, wherein the micro level health is estimated at a plant level; and updating the macro level health of the each plant in the sample set of plants based on the corresponding micro level health.

10. The non-transitory computer readable medium as claimed in claim 9, wherein the non-transitory computer readable medium estimates the macro level health for each of the plurality of clusters by:

identifying a plurality of indices corresponding to plants in each of the plurality of clusters, via the one or more hardware processors;

generating a health index value for the at least one SoS information based on value of each of the plurality of indices, via the one or more hardware processors;

comparing the health index value with a threshold range of reference data, via the one or more hardware processors; and estimating the macro level health of each of the plurality of clusters of plants based on the comparison of the health index value with the threshold range of reference data, via the one or more hardware processors, wherein the health index values are normalized between 0 and 1, and wherein the micro level health is estimated as indicating poor health when the health index values are closer to 0, and the micro level health is estimated as indicating good health when the health index values are closer to 1.

11. The non-transitory computer readable medium as claimed in claim 9, wherein the non-transitory computer readable medium estimates the micro level health by:

identifying at least one sensor which is to be considered, based on a plant type information pertaining to the plants in the sample set of plants, via the one or more hardware processors;

identifying a weightage to be assigned to data from the at least one sensor, based on the plant type information and data pertaining to growth stage of the plants in the sample set of plants, via the one or more hardware processors; and estimating the micro level health of each plant in the sample set of plants, based on the weightage assigned to each of the plurality of parameters, via the one or more hardware processors.

12. The non-transitory computer readable medium as claimed in claim 9, wherein the growth stage of the sample set of plants comprises Transplanting, Tillering, Panicle initiation, Flowering and up to harvesting.

\* \* \* \* \*